(12) United States Patent
Gelbin et al.

(10) Patent No.: US 7,442,732 B2
(45) Date of Patent: Oct. 28, 2008

(54) HINDERED AMINE LIGHT STABILIZERS COMPRISING NEOALKANEDIOL PHOSPHITES

(75) Inventors: Michael E. Gelbin, Middlebury, CT (US); Carloss L. Gray, Fairmont, WV (US)

(73) Assignee: Crompton Corporation, Middlebury, CT (US)

( * ) Notice: Subject to any disclaimer, the term of this patent is extended or adjusted under 35 U.S.C. 154(b) by 556 days.

(21) Appl. No.: 11/093,434

(22) Filed: Mar. 29, 2005

(65) Prior Publication Data

US 2006/0223918 A1    Oct. 5, 2006

(51) Int. Cl.
 *C08K 5/3435*    (2006.01)
 *C07F 9/06*    (2006.01)
(52) U.S. Cl. ......................... 524/99; 546/25
(58) Field of Classification Search ............ 524/99; 546/25
 See application file for complete search history.

(56) References Cited

U.S. PATENT DOCUMENTS

| | | | |
|---|---|---|---|
| 3,467,733 A | 9/1969 | Dever et al. | 260/927 |
| 3,600,168 A * | 8/1971 | Lawton | 430/138 |
| 3,714,302 A | 1/1973 | Dever et al. | 260/976 |
| 4,096,114 A | 6/1978 | Minagawa et al. | 260/45.8 |
| 4,808,645 A * | 2/1989 | Ravichandran et al. | 524/99 |
| 5,239,076 A | 8/1993 | Meier et al. | 546/187 |
| 5,424,348 A | 6/1995 | Mahood | 524/117 |
| 5,594,053 A | 1/1997 | Avakian et al. | 524/120 |
| 5,607,989 A | 3/1997 | Bishop et al. | 524/102 |
| 5,616,636 A | 4/1997 | Avar et al. | 524/102 |
| 5,618,866 A | 4/1997 | Prabhu et al. | 524/117 |
| 5,623,009 A | 4/1997 | Mahood | 524/117 |
| 5,654,430 A | 8/1997 | Pitteloud | 546/24 |
| 5,986,098 A * | 11/1999 | Staniek | 546/25 |
| 2002/0042538 A1* | 4/2002 | Yoneda et al. | 560/209 |

FOREIGN PATENT DOCUMENTS

| | | |
|---|---|---|
| DE | 2905808 | 2/1979 |
| DE | 290906 | 12/1988 |

OTHER PUBLICATIONS

Chmela et al., Hals-phosphite combinations as light and heat stabilizers for polypropylene Polymer Degradation and Stability, 39 (1993) pp. 367-371.

* cited by examiner

*Primary Examiner*—Kriellion A Sanders
(74) *Attorney, Agent, or Firm*—Jamies Sher

(57) ABSTRACT

Disclosed herein are compounds of the structure:

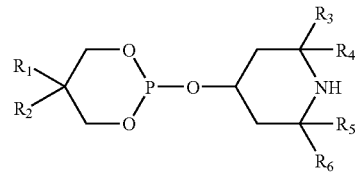

wherein $R_1$, $R_2$, $R_3$, $R_4$, $R_5$, and $R_6$ are independently selected alkyl groups, provided that $R_1$ is different from $R_2$. The compounds are useful as stabilizers for thermoplastic resins.

17 Claims, No Drawings

HINDERED AMINE LIGHT STABILIZERS COMPRISING NEOALKANEDIOL PHOSPHITES

BACKGROUND OF THE INVENTION

1. Field of the Invention

The present invention relates to a novel phosphite antioxidant for polymeric resin compositions, and more particularly relates to stabilized resin compositions and stabilizer concentrates for resin compositions.

2. Description of Related Art

Phosphite stabilizer compositions comprising 2,2,6,6-tetramethylpiperidin-4-ol, reportedly a Hindered Amine Light Stabilizer (HALS) building block, are known in the art.

U.S. Pat. No. 3,467,733 discloses cyclic phosphites and diphosphites, such as bis(1,3,2-di-oxaphosphorinanyl-2-oxy)aryl alkanes and mono- and bis(1,3,2-di-oxaphosphorinanyl-2-oxy)benzenes, that are said to be useful as stabilizers for organic compositions, such as rubber and polyvinyl chloride, and are made by reacting a cyclic phosphorohalidite with a hydroxy aromatic compound, subsequently neutralizing the reaction product with a nitrogen-containing compound, such as ammonia, and recovering the desired phosphite or diphosphite.

U.S. Pat. No. 3,714,302 discloses cyclic phosphites that are produced by reacting phenol in the melt with a crude reaction product or $PCl_3$ and a 2,2-di-lower alkyl-1,3-propane glycol and recovering the desired product by distillation. The cyclic phosphites are said to be useful as stabilizers for organic compositions, such as rubber and polyvinyl chloride.

U.S. Pat. No. 4,096,114 discloses organic phosphites having at least one 2,2,6,6-tetramethyl piperidyl substituent attached at the 4-position to phosphorus through oxygen, and at least one polyol or polyphenol group, which are said to be superior light and heat stabilizers for organic polymeric materials, such as polyethylene, polypropylene, polyvinyl chloride, acrylonitrile-butadiene-styrene terpolymers, polyamides, polystyrene, and similar polymers.

U.S. Pat. Nos. 5,424,348 and 5,623,009 disclose a phosphite having the formula:

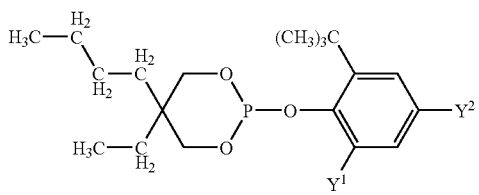

wherein $Y^1$ is an alkyl group and $Y^2$ is selected from the group consisting of sec-butyl and tert-butyl. The phosphite is said to exhibit enhanced stability including hydrolytic and UV stability, and to be useful in stabilizing thermoplastic compositions.

U.S. Pat. No. 5,594,053 discloses a stabilized thermoplastic composition comprising a stabilizing amount of a phosphite of the formula:

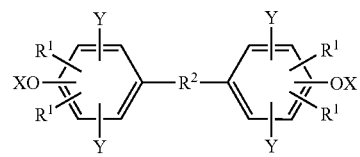

$R^1$ is independently selected from the group consisting of alkyl groups having from 1 to 9 carbon atoms, Y is independently selected from the group consisting of hydrogen, halogen, or alkyl; and the —O—X groups are positioned at the respective ortho- or para- positions with respect to the diphenyl linkage, the remaining ortho- and para- positions with respect to the —O—X linkage being occupied by $R^1$ whereby the —O—X groups are hindered by the presence of at least one $R^1$ group; $R^2$ group is a divalent alkylidene radical having from 1 to 6 carbon atoms or a direct bond; and wherein X has the formula:

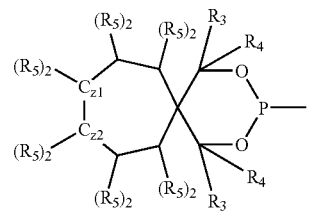

z1 and z2 can be 0 or 1; and $R_3$, $R_4$ and $R_5$ are independently selected from the group consisting of hydrogen, halogen, or alkyl.

U.S. Pat. No. 5,607,989 discloses a piperidinyl phosphite composition consisting of a piperidinyl phosphite compound and an additive having a melting point of greater than 155° C. selected from the group consisting of (i) sorbitol compounds, (ii) phosphite compounds and (iii) sterically hindered phenolic compounds, and polyolefin compositions containing them.

U.S. Pat. No. 5,616,636 discloses a composition comprising: a) a compound containing a phosphite or phosphonite group and at least one 2,2,6,6-tetraalkylpiperidinyl group, and b) a polyolefin which has been produced in the presence of a catalyst which is either i) a supported Ziegler catalyst or ii) a metallocene catalyst, from which polyolefin the catalyst has not been removed.

U.S. Pat. No. 5,618,866 discloses a phosphite and stabilized thermoplastic composition comprising the phosphite where the phosphite has the formula:

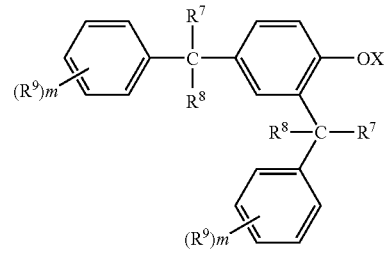

In the above compound, $R^7$ and $R^8$ are preferably alkyl of from 1 to 6 carbon atoms, $R^9$ is preferably alkyl of 1 to 12 carbon atoms, m is from 0 to 5. The dicumyl group includes the OX groups which are the phosphite portion. The OX group is hindered by only one alkylaryl group at the ortho position with the other ortho position being occupied by hydrogen. X has the following formula:

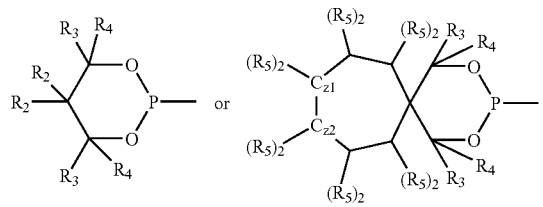

wherein $R_2$ is independently selected from the group consisting of alkyl groups having from 1 to 12 carbon atoms, z1 and z2 can be 0 or 1, and $R_3$, $R_4$ and $R_5$ are independently selected from the group consisting of hydrogen, halogen, or alkyl of from 1 to 3 carbon atoms.

U.S. Pat. No. 5,654,430 discloses oligomeric compounds of the formula I

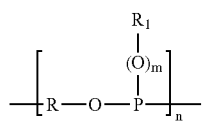

in which R is a group of the formula

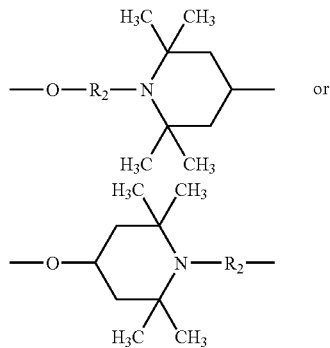

where the oxygen in the group R is in each case bonded to the phosphorus in the recurring structural units and the radical $R_2$ or the carbon in the 4-position of the piperidinyl ring in the group R is in each case bonded to the oxygen in the recurring structural units; and $R_1$ is $C_1$-$C_{25}$ alkyl, $C_2$-$C_{25}$ alkyl which is interrupted by oxygen, sulfur or >N—$R_3$; $C_2$-$C_{24}$ alkenyl, unsubstituted or $C_1$-$C_4$ alkyl-substituted $C_5$-$C_{15}$ cycloalkyl; unsubstituted or $C_1$-$C_4$ alkyl-substituted $C_5$-$C_{15}$ cycloalkenyl; $C_7$-$C_9$ phenyl alkyl which is unsubstituted or substituted on the phenyl ring by $C_1$-$C_4$ alkyl; or tetrahydroabietyl, $R_2$ is $C_1$-$C_{18}$ alkylene, $C_2$-$C_{28}$ alkylene which is interrupted by oxygen, sulfur or >N—$R_3$; $C_4$-$C_8$ alkenylene or phenylethylene, R3 is hydrogen or $C_1$-$C_8$ alkyl, m is 0 or 1, and n is a number from 2 to 25, where the group R, the radicals $R_1$, $R_2$ and $R_3$ and the index m are identical or different in the recurring structural units of the formula. The compounds are said to be useful as stabilizers for organic materials against oxidative, thermal or light-induced degradation.

East German 290906 discloses olefins stabilized against thermo- and photooxidative degradation with phosphite and phosphonite esters based on hindered amino alcohols and phenols or in the form of 1,3,2-dioxaphosphorus heterocyclic compounds. Thus, isotactic polypropylene containing bis(2,2,6,6-tetramethyl-4-piperidinyl) 2,6-di-tert-butyl-4-methylphenyl phosphite (I) at 180° C. had an autoxidation inductive period greater than 1000 minutes, compared to 47 minutes in the absence of (I) or 410 minutes in the presence of a BHT control.

DEOS 2,905,808 discloses the preparation of a phosphite comprising 2,2,6,6-tetramethylpiperidin-4-ol and pentaerythritol in a three-step reaction.

Chmela, S. et al., Polymer Degradation and Stability 39:367-371(1993) disclosed the use of organic phosphites combined with HALS "as stabilizers in the photo- and thermoxidation of polypropylene film. The efficiency of the mixture of HALS and phosphite was compared with the efficiency of the combination of HALS and phosphite in one molecule. A strong synergistic effect was observed for the molecule with HALS and phosphite moieties. Generally, the mixture of HALS and phosphite exhibited synergistic, antagonistic or additive effects. The efficiency of the mixture depends upon the chemical structure of the phosphite and HALS structural units as well as on the ratio of the components."

Thus, it is seen that organic phosphites are known in the art as secondary antioxidants and costabilizers for polyolefins. Additional examples of such known phosphites are given in H. Zweifel (Ed) Plastics Additives Handbook, 5th edition, Hanser Publishers, Munich 2000. However, there continues to be a demand for an effective phosphite stabilizer for organic materials that are sensitive to oxidative, heat, and/or light-induced degradation. There also continues to be a demand for such a stabilizer to be available in liquid form and for a phosphite stabilizer containing a HALS structural unit.

The disclosures of the foregoing are incorporated herein by reference in their entirety.

SUMMARY OF THE INVENTION

As noted above, the present invention relates to a novel phosphite antioxidant and to stabilized resin compositions and stabilizer concentrates comprising the antioxidant for resin compositions.

In one aspect, the present invention relates to a compound having the structure:

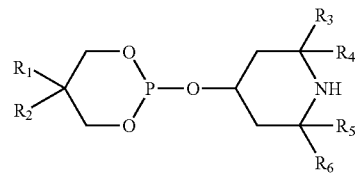

wherein $R_1$, $R_2$, $R_3$, $R_4$, $R_5$, and $R_6$ are independently selected alkyl groups, provided that $R_1$ is different from $R_2$.

It will be noted that this compound contains both a HALS and a neoalkanediol structural unit and, depending on the identities of $R_1$, $R_2$, $R_3$, $R_4$, $R_5$, and $R_6$, can exist in liquid form at room temperature.

In another aspect, the present invention relates to a stabilized composition comprising:

(A) a thermoplastic resin, and (B) a stabilizing amount of:

(1) a compound having the structure:

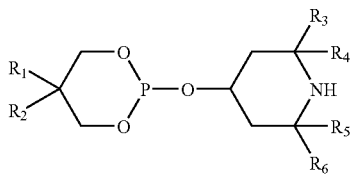

wherein $R_1$, $R_2$, $R_3$, $R_4$, $R_5$, and $R_6$ are independently selected alkyl groups, provided that $R_1$ is different from $R_2$ and, optionally, (2) a co-stabilizer selected from the group consisting of phenolics, aromatic amines, hydroxylamines, alkylamine-N-oxides, lactones, and thioethers.

In still another aspect, the present invention relates to a method for stabilizing a thermoplastic resin comprising adding to said resin a stabilizing amount of a stabilizer having the structure:

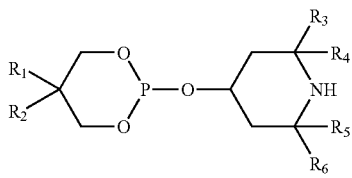

wherein $R_1$, $R_2$, $R_3$, $R_4$, $R_5$, and $R_6$ are independently selected alkyl groups, provided that $R_1$ is different from $R_2$. Generally, a "stabilizing amount" of the compound will be from about 0.01 to about 2 parts phr, preferably, from about 0.01 to about 1 part phr, more preferably, from about 0.01 to about 0.2 part phr.

In yet another aspect, the present invention relates to a method for the preparation of stabilizer having the structure:

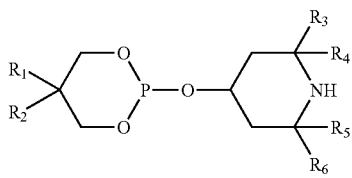

wherein $R_1$, $R_2$, $R_3$, $R_4$, $R_5$, and $R_6$ are independently selected alkyl groups, provided that $R_1$ is different from $R_2$ wherein the method comprises reacting a phosphorous trihalide with a tetraalkylpiperidinol and a 2,2-disubstituted propanediol.

DESCRIPTION OF THE PREFERRED EMBODIMENT(S)

The compounds employed in the practice of this invention are of the structure:

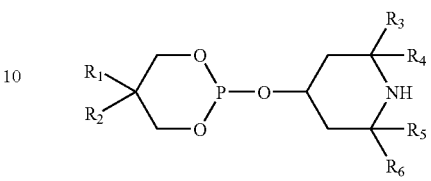

wherein $R_1$, $R_2$, $R_3$, $R_4$, $R_5$, and $R_6$ are independently selected alkyl groups, provided that $R_1$ is different from $R_2$. Such alkyl groups can be either straight chain or branched chain and preferably comprise from one to eight carbon atoms, e.g. methyl, ethyl, propyl, butyl, pentyl, hexyl, heptyl, octyl, isomers of the foregoing, and the like. More preferably, $R_1$ and $R_2$ comprise from one to six carbon atoms and $R_3$, $R_4$, $R_5$, and $R_6$ comprise from one to four carbon atoms.

Most preferably, $R_1$ is ethyl, $R_2$ is butyl, and $R_3$, $R_4$, $R_5$, and $R_6$ are each methyl.

The compounds of the present invention can be prepared by reacting a phosphorous trihalide, e.g., phosphorous trichloride, with a tetraalkylpiperidinol, e.g., 2,2,6,6-tetramethylpiperidin-4-ol, and a 2,2-disubstituted propanediol. In a preferred embodiment, the propanediol is the first component to react with the phosphorous trihalide, yielding the corresponding halophosphite. The halophosphite is then reacted with the tetraalkylpiperidinol to provide the desired product. A base, such as a non-nucleophilic tertiary amine, may, if desired, be employed to promote either reaction step.

The present invention also comprises a stabilized polymer composition that includes an effective amount of the phosphite described above. An amount of the phosphite of the invention is considered to be an "effective amount" when the polymer composition containing the phosphite of the invention shows improved stability in any of its physical or color properties in comparison to an analogous polymer composition that does not include a phosphite of the invention. In most polymer compositions, however, it will be preferred that the phosphites be present in an amount equal to about 0.01 to about 2 parts by weight per 100 parts by weight resin (phr). Amounts of about 0.01 to about 1 phr are more preferred, about 0.01 to about 0.2 most preferred.

The polymer may be any thermoplastic known in the art, such as polyesters, polyurethanes, polyalkylene terephthalates, polysulfones, polyimides, polyphenylene ethers, styrenic polymers, polycarbonates, acrylic polymers, polyamides, polyacetals, halide containing polymers and polyolefin homopolymers and copolymers. Mixtures of different polymers, such as polyphenylene ether/styrenic resin blends, polyvinyl chloride/ABS or other impact modified polymers, such as methacrylonitrile and a-methylstyrene containing ABS, and polyester/ABS or polycarbonate/ABS and polyester plus some other impact modifier may also be used. Such polymers are available commercially or may be made by means well known in the art.

Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example, high density polyethylene (HDPE), low density polyethylene (LDPE) and linear low density polyethylene (LLDPE) may be employed in the practice of the present invention. Mixtures of these polymers, for example, mixtures of polypropylene with polyisobutylene, polypropylene with polyethylene (for example, PP/HDPE, PP/LDPE) and mixtures of different types of polyethylene (for example, LDPE/HDPE), may also be used. Also useful are copolymers of monoolefins and diolefins with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene, or ethylidene-norbornene; as well as mixtures of such copolymers and their mixtures with polymers mentioned above, for example, polypropylene/ethylene propylene-copolymers, LDPE/EVA, LDPE/EAA, LLDPE/EVA and LLDPE/EAA.

The thermoplastic polymers employed in the practice of the present invention may also be styrenic polymers, such as polystyrene, poly-(p-methylstyrene), poly-(α-methylstyrene), copolymers of styrene or a-methylstyrene with dienes or acrylic derivatives, such as, for example, styrene/butadiene, styrene/acrylonitrile, styrene/alkyl methacrylate, styrene/maleic anhydride, styrene/butadiene/ethylacrylate/styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/-butadiene/styrene, styrene/isoprene/styrene, styrene/ethylene/butylene/styrene or styrene/ethylene/propoylene styrene. Styrenic polymers may additionally or alternatively include graft copolymers of styrene or α-methylstyrene such as, for example, styrene on polybutadiene, styrene on polybutadiene-styrene or polybutadieneacrylonitrile; styrene and acrylonitrile (or methacrylonitrile) on polybutadiene and copolymers thereof, styrene and maleic anhydride or maleimide on polybutadiene; sytrene, acrylonitrile, and maleic anhydride or maleimide on polybutadiene; styrene, acrylonitrile, and methyl methacrylate on polybutadiene, styrene and alkyl acrylates or methacrylates on polybutadiene, styrene and acrylonitrile on ethylene/-propylene/diene terpolymers, styrene and acrylonitrile on polyacrylates or polymethacrylates, styrene and acrylonitrile on acrylate/butadiene copolymers, and the like.

Nitrile polymers are also useful in the polymer composition of the invention. These include homopolymers and copolymers of acrylonitrile and its analogs, such as polymethacrylonitrile, polyacrylonitrile, acrylonitrile/-butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide, and methacrylamide may also be used.

Halogen-containing polymers may also be useful. These include resins such as polychloroprene, epichlorohydrin homo-and copolymers, polyvinyl chloride, polyvinyl bromide, polyvinyl fluoride, polyvinylidene chloride, chlorinated polyethylene, chlorinated polypropylene, florinated polyvinylidene, brominated polyethylene, chlorinated rubber, vinyl chloride-vinylacetate copolymers, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride tercopolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate terpolymer, vinyl chloride-acrylic acid ester copolymers, vinyl chloride-maleic acid ester copolymers, vinyl chloride-methacrylic acid ester copolymers, vinyl chloride-acrylonitrile copolymer, and internally plasticized polyvinyl chloride.

Other useful thermoplastic polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-2(2,2,4(4-hydroxyphenyl)-propane) terephthalate and polyhydroxybenzoates as well as block-copolyetheresters derived from polyethers having hydroxyl end groups.

Polyamides and copolyamides which are derived from diamines and dicarboxylic acids and/or from aminocarboxylic acids or the corresponding lactams, such as polyamide, 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic or/and terephthalic acid and optionally an elastomer as modifier, for example poly-2,4,4-trimethylhexamethylene terephthalamide or poly-m-phenylene isophthalamide may be useful. Further copolymers of the aforementioned polyamides with polyolefins, olefin copolymers, ionomers, or chemically bonded or grafted elastomers; or with polyethers, such as for instance, with polyethylene glycol, polypropylene glycol, or polytetramethylene glycols and polyamides or copolyamides modified with EPDM or ABS may be used.

Polyolefin, polyalkylene terephthalate, polyphenylene ether and styrenic resins, and mixtures thereof are more preferred, with polyethylene, polypropylene, and mixtures thereof being particularly preferred.

Phenolics that can be employed as optional co-stabilizers in the practice of the present invention include, but are not limited to:

1. Alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6 dimethylphenol, 2,6-di-octadecyl-4-methylphenol, 2,4,6,-tricyclohexyphenol, 2,6-di-tert-butyl-4-methoxymethylphenol.

2. Alkylated hydroquinones, for example, 2,6-di-tert-butyl-4-methoxyphenol, 2,5-di-tert-butyl-hydroquinone, 2,5-di-tert-amylhydroquinone, 2,6-diphenyl-4-octadecyloxyphenol.

3. Hydroxylated thiodiphenyl ethers, for example, 2,2'-thio-bis-(6-tert-butyl-4-methylphenol), 2,2'-thio-bis-(4-octylphenol), 4,4'-thio-bis-(6-tert-butyl-3-methylphenol), 4,4'-thio-bis-(6-tert-butyl-2-methylphenol).

4. Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl(phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(α-methylbenzyl)-4-nonylphenol), 2,2'-methylene-bis-(6-(α,α-dimethylbenzyl)-4-nonyl-phenol), 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane, 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy-5-methylphenyl)-dicyclopentadiene, di-(2-(3'-tert-butyl-2'hydroxy-5'methylbenzyl)-6-tert-butyl-4-methylphenyl )terephthalate, and other phenolics such as mono-acrylate esters of bisphenols such as ethylidiene bis-2,4-di-t-butyl phenol monoacrylate ester.

5. Benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercaptoacetate, bis-(4-tert-butyl-3-hydroxy-2,6-dimethylbenzyl)dithiol-terephthalate, 1,3,5-tris-(3,5-di-tert-butyl-4-hydroxybenzyl)isocyanurate, 1,3,5-tris-(4-tert-butyl-3-hydroxy-2,6-dimethylbenzyl) isocyanurate, dioctadecyl 3,5-di-tert-butyl-4-hydroxybenzyl-phosphonate, calcium salt of monoethyl 3,5-di-tert-butyl-4-hydroxybenzylphosphonate, 1,3,5-tris-(3,5-dicyclohexyl-4-hydroxybenzyl) isocyanurate.

6. Acylaminophenols, for example, 4-hydroxy-lauric acid anilide, 4-hydroxy-stearic acid anilide, 2,4-bis-octylmercapto-6-(3,5-tert-butyl-4-hydroxyanilino)-s-triazine, octyl-N-(3,5-di-tert-butyl-4-hydroxyphenyl)carbamate.

7. Esters of β-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, di-hydroxyethyl oxalic acid diamide.

8. Esters of β-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thidiethyleneglycol, dihydroxyethyl oxalic acid diamide.

9. Esters of β-(5-tert-butyl-4-hydroxy-3-methylphenyl) propionic acid with mono- or polyhydric alcohols, e.g., with methanol, diethylene glycol, octadecanol, triethylene glycol, 1,6-hexanediol, pentaerythritol, neopentyl glycol, tris(hydroxyethyl) isocyanurate, thiodiethylene glycol, N,N-bis(hydroxyethyl) oxalic acid diamide.

10. Amides of β-(3,5-di-tert-butyl-4-hydroxyphenol)-propionic acid for example, N,N'-di-(3,5-di-tert-butyl-4-hydroxyphenylpropionyl)-hexamethylen-diamine, N,N'-di-(3,5-di-tert-butyl-4-hydroxyphenylpropionyl)trimethylenediamine, N,N'-di-(3,5-di-tert-butyl-4-hydroxyphenylpropionyl)-hydrazine.

Aromatic amines that are useful in the practice of the present invention can be represented by the general formula

$R^1$—NH—$R^2$ where $R^1$ and $R^2$ may be, but are not necessarily, identical. Thus, in a preferred embodiment, $R^1$ and $R^2$ can be independently selected from the group consisting of (i) aromatic carbon, (ii) aliphatic $R^1$ and aromatic $R^2$ carbon atoms, and (iii) aromatic carbon linked to a second nitrogen atom to give a phenylene diamine.

Where $R^1$ is aliphatic, it can be straight chain or branched and can have from one to twelve carbon atoms, e.g., methyl, ethyl, propyl, butyl, pentyl, hexyl, heptyl, octyl, nonyl, decyl, undecyl, dodecyl, and isomers thereof. It is preferred that, where $R^1$ is aliphatic, it be a straight or branched chain aliphatic group having from one to eight carbon atoms, and more preferred that it have from one to four carbon atoms.

The amine antioxidants can be hydrocarbon substituted diarylamines, such as, aryl, alkyl, alkaryl, and aralkyl substituted diphenylamine antioxidant materials. A nonlimiting list of commercially available hydrocarbon substituted diphenylamines includes substituted octylated, nonylated, and heptylated diphenylamines and para-substituted styrenated ora-methyl styrenated diphenylamines. The sulfur-containing hydrocarbon substituted diphenylamines, such as p-(p-toluenesulfonylamido)-diphenylamine, i.e.,

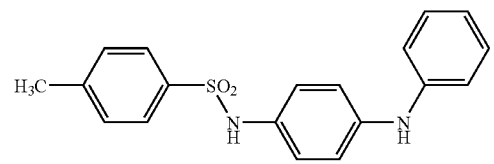

are also considered as part of this class.

Hydrocarbon-substituted diarylamines that are useful in the practice of this invention can be represented by the general formula Ar—NH—Ar' wherein Ar and Ar' are independently selected aryl radicals, at least one of which is preferably substituted with at least one alkyl radical. The aryl radicals can be, for example, phenyl, biphenyl, terphenyl, naphthyl, anthryl, phenanthryl, and the like. The alkyl substituent(s) can be, for example, methyl, ethyl, propyl, butyl, pentyl, hexyl, heptyl, octyl, nonyl, decyl, isomers thereof, and the like.

Preferred hydrocarbon-substituted diarylamines are those disclosed in U.S. Pat. Nos. 3,452,056 and 3,505,225, the disclosures of which are incorporated by reference herein. The preferred hydrocarbon-substituted diarylamines can be represented by the following general formulas:

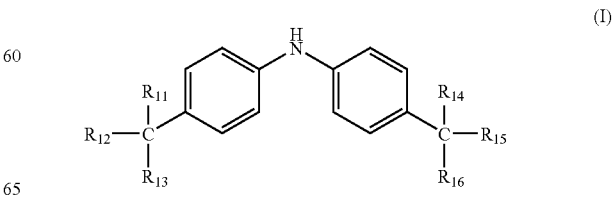

(I)

where $R_{11}$ is selected from the group consisting of phenyl and p-tolyl radicals;

$R_{12}$ and $R_{13}$ are independently selected from the group consisting of methyl, phenyl, and p-tolyl radicals;

$R_{14}$ is selected from the group consisting of methyl, phenyl, p-tolyl, and neopentyl radicals;

$R_{15}$ is selected from the group consisting of methyl, phenyl, p-tolyl, and 2-phenylisobutyl radicals; and, $R_{16}$ is a methyl radical.

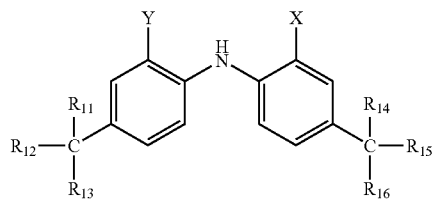
(II)

where $R_{11}$ through $R_{15}$ are independently selected from the radicals shown in Formula I and $R_{17}$ is selected from the group consisting of methyl, phenyl, and p-tolyl radicals;

X is a radical selected from the group consisting of methyl, ethyl, $C_3$-$C_{10}$ sec-alkyl, α,α-dimethylbenzyl, α-methylbenzyl, chlorine, bromine, carboxyl, and metal salts of the carboxylic acids where the metal is selected from the group consisting of zinc, cadmium, nickel, lead, tin, magnesium, and copper; and, Y is a radical selected from the group consisting of hydrogen, methyl, ethyl, $C_3$-$C_{10}$ sec-alkyl, chlorine, and bromine.

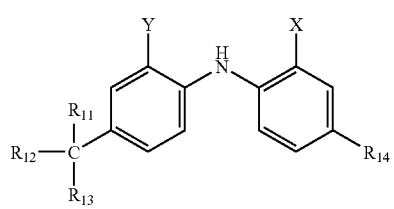
(III)

where $R_{11}$ is selected from the group consisting of phenyl or p-tolyl radicals;

$R_{12}$ and $R_{13}$ are independently selected from the group consisting of methyl, phenyl, and p-tolyl radicals;

$R_{14}$ is a radical selected from the group consisting of hydrogen, $C_3$-$C_{10}$ primary, secondary, and tertiary alkyl, and $C_3$-$C_{10}$ alkoxyl, which may be straight chain or branched; and X and Y are radicals selected from the group consisting of hydrogen, methyl, ethyl, $C_3$-$C_{10}$ sec-alkyl, chlorine, and bromine.

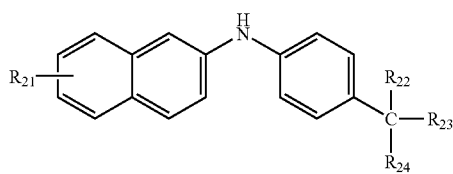
(IV)

where $R_{18}$ is selected from the group consisting of phenyl and p-tolyl radicals;

$R_{19}$ is a radical selected from the group consisting of methyl, phenyl, p-tolyl and 2-phenyl isobutyl; and $R_{20}$ is a radical selected from the group consisting of methyl, phenyl, and p-tolyl.

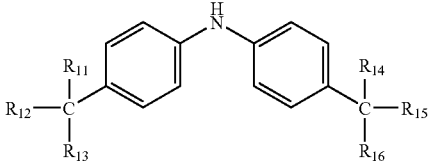
(V)

where $R_{21}$ is selected from the group consisting of hydrogen, α,α-dimethylbenzyl, α-methylbenzhydryl, triphenylmethyl, and α,α p-trimethylbenzyl radicals;

$R_{22}$ is selected from the group consisting of phenyl or p-tolyl radicals;

$R_{23}$ is selected from the group consisting of methyl, phenyl, and p-tolyl radicals; and $R_{24}$ is selected from the group consisting of methyl, phenyl, p-tolyl, and 2-phenylisobutyl radicals.

Typical chemicals useful in the invention are as follows:

TYPE I

| $R_{11}$ | $R_{12}$ | $R_{13}$ | $R_{14}$ | $R_{15}$ | $R_{16}$ |
|---|---|---|---|---|---|
| Phenyl | Methyl | Methyl | Phenyl | Methyl | Methyl |
| Phenyl | Phenyl | Methyl | Phenyl | Phenyl | Methyl |
| Phenyl | Phenyl | Phenyl | Neopentyl | Methyl | Methyl |
| p-Tolyl | Methyl | Methyl | p-Tolyl | Methyl | Methyl |

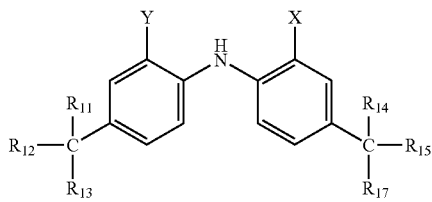

TYPE II

| $R_{11}$ | $R_{12}$ | $R_{13}$ | $R_{14}$ | $R_{15}$ | $R_{17}$ | X | Y |
|---|---|---|---|---|---|---|---|
| Phenyl | Methyl | Methyl | Phenyl | Methyl | Methyl | α,α-Dimethyl-benzyl | Hydrogen |
| Phenyl | Methyl | Methyl | Phenyl | Methyl | Methyl | Bromo | Bromo |
| Phenyl | Methyl | Methyl | Phenyl | Methyl | Methyl | Carboxyl | Hydrogen |
| Phenyl | Methyl | Methyl | Phenyl | Methyl | Methyl | Nickel carboxylate | Hydrogen |
| Phenyl | Methyl | Methyl | Phenyl | Methyl | Methyl | 2-Butyl | Hydrogen |
| Phenyl | Methyl | Methyl | Phenyl | Methyl | Methyl | 2-Octyl | Hydrogen |
| Phenyl | Phenyl | Phenyl | Phenyl | Phenyl | Phenyl | 2-Hexyl | Hydrogen |

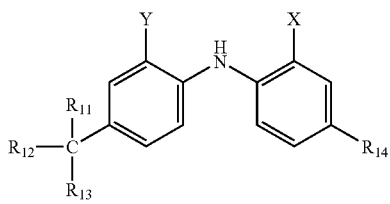

TYPE III

| $R_{11}$ | $R_{12}$ | $R_{13}$ | $R_{14}$ | X | Y |
|---|---|---|---|---|---|
| Phenyl | Methyl | Methyl | Isopropoxy | Hydrogen | Hydrogen |
| Phenyl | Methyl | Methyl | Hydrogen | 2-Octyl | Hydrogen |
| Phenyl | Phenyl | Phenyl | Hydrogen | 2-Hexyl | Hydrogen |

Of the foregoing preferred hydrocarbon-substituted diarylamines, the substituted diphenylamines of the formula:

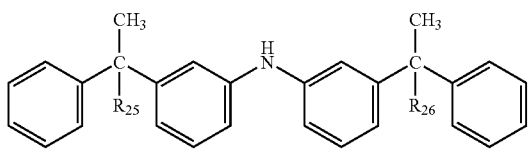

where $R_{25}$ and $R_{26}$ are methyl or phenyl are especially preferred. The compound wherein $R_{25}$ and $R_{26}$ are both methyl is 4,4'-bis(α,α-dimethylbenzyl)diphenylamine and the compound wherein $R_{25}$ and $R_{26}$ are both phenyl is 4,4'-bis(α-methylbenzyl)diphenylamine.

A second class of amine antioxidants comprises the reaction products of a diarylamine and an aliphatic ketone. The diarylamine aliphatic ketone reaction products that are useful herein are disclosed in U.S. Pat. Nos. 1,906,935; 1,975,167; 2,002,642; and 2,562,802. Briefly described, these products are obtained by reacting a diarylamine, preferably a diphenylamine, which may, if desired, possess one or more substituents on either aryl group, with an aliphatic ketone, preferably acetone, in the presence of a suitable catalyst. In addition to diphenylamine, other suitable diarylamine reactants include dinaphthyl amines; p-nitrodiphenylamine; 2,4-dinitrodiphenylamine; p-aminodiphenylamine; p-hydroxydiphenylamine; and the like. In addition to acetone, other useful ketone reactants include methylethylketone, diethylketone, monochloroacetone, dichloroacetone, and the like.

A preferred diarylamine-aliphatic ketone reaction product is obtained from the condensation reaction of diphenylamine and acetone (NAUGARD A, Crompton Corporation), for example, in accordance with the conditions described in U.S. Pat. No. 2,562,802. The commercial product is supplied as a light tan-green powder or as greenish brown flakes and has a melting range of 85° to 95° C.

A third class of suitable amines comprises the N,N' hydrocarbon substituted p-phenylene diamines. The hydrocarbon substituent may be alkyl or aryl groups, which can be substituted or unsubstituted. As used herein, the term "alkyl," unless specifically described otherwise, is intended to include cycloalkyl. Representative materials are:

N-phenyl-N'-cyclohexyl-p-phenylenediamine;
N-phenyl-N'-sec-butyl-p-phenylenediamine;
N-phenyl-N'-isopropyl-p-phenylenediamine;
N-phenyl-N'-(1,3-dimethylbutyl)-p-phenylenediamine;
N,N'-bis-(1,4-dimethylpentyl)-p-phenylenediamine;
N,N'-diphenyl-p-phenylenediamine;
N,N'-di-beta naphthyl-p-phenylenediamine; mixed diaryl-p-N,N'-bis-(1-ethyl-3-methylpentyl)-p-phenylenediamines; and
N,N'-bis-(1 methylheptyl)-p-phenylenediamine.

A fourth class of amine antioxidants comprises materials based on quinoline, especially, polymerized 1,2-dihydro-2,2,4-trimethylquinoline (Naugard Super Q, Crompton Corporation). Representative materials also include 6-dodecyl-2,2,4-trimethyl-1,2-dihydroquinoline; 6-ethoxy-2,2,4-trimethyl-1-2-dihydroquinoline, and the like.

Secondary amines that are especially preferred for use in the practice of the present invention are 4,4'-bis(a,a dimethylbenzyl)diphenylamine (Naugard 445, Crompton Corporation), octylated diphenylamine (Naugard Octamine, Crompton Corporation), polymerized 1,2-dihydro-2,2,4-trimethylquinoline (Naugard Super Q, Crompton Corporation) and p-(p-toluene-sulfonylamido)-diphenyl amine (Naugard S A, Crompton Corporation).

Lactones that can be employed as co-stabilizers in the practice of the present invention include those of the structure

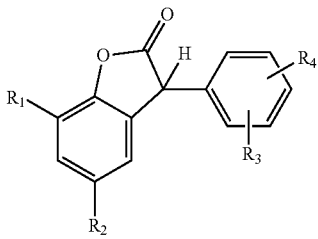

wherein

R₁ and R₂ are independently selected from the group consisting of hydrogen; chloro; hydroxy; $C_1$-$C_{25}$ alkyl; $C_7$-$C_9$-phenylalkyl; unsubstituted or $C_1$-$C_4$ alkyl-substituted phenyl; unsubstituted or $C_1$-$C_4$ alkyl-substituted $C_5$-$C_8$ cycloalkyl; $C_1$-$C_{18}$ alkoxy; $C_1$-$C_{18}$ alkylthio; $C_1$-$C_4$ alkylamino; di-($C_1$-$C_4$ alkyl)amino; $C_1$-$C_{25}$ alkanoyloxy; $C_1$-$C_{25}$ alkanoylamino; $C_3$-$C_{25}$ alkenoyloxy; $C_3$-$C_{25}$ alkanoyloxy which is interrupted by oxygen, sulfur, or >N—R₈; $C_6$-$C_9$ cycloalkylcarbonyloxy; benzoyloxy or $C_1$-$C_{12}$ alkyl-substituted benzoyloxy;

R₈ is hydrogen or $C_1$-$C_8$ alkyl; and

R₃ and R₄ are independently selected from the group consisting of hydrogen, $C_1$-$C_8$ alkyl, $C_1$-$C_4$ alkoxy, halogen, a group

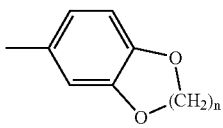

in which n is 1 or 2, or a group

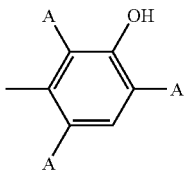

in which the radicals A are independently selected from the group consisting of $C_1$-$C_8$ alkyl and $C_1$-$C_8$ alkoxy.

A particularly useful representative of these lactones is 5,7-di-t-butyl-3-(3,4,-dimethylphenyl)-3H-benzofuran-2-one, which is of the structure

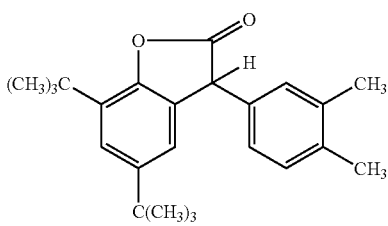

This compound is commercially available from Ciba Specialties as HP 136.

Thioethers that are useful as co-stabilizers in the practice of the present invention can be of the structure:

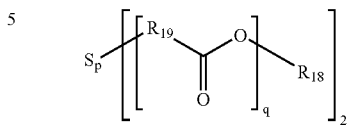

where p is 1 or 2, q is 0 or 1, and p+q=2, $R_{18}$ is a straight or branched chain alkyl moiety of 1 to 20 carbon atoms, and $R_{19}$ is a straight or branched chain alkylene moiety of 1 to 8 carbon atoms. Thus, $R_{18}$ can, for example, be methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, and isomers thereof, and $R_{19}$ can, for example, be methylene, ethylene, propylene, butylene, pentylene, hexylene, heptylene, octylene, and isomers thereof. It is preferred that $R_{18}$ be a straight or branched chain alkyl moiety of 8 to 18 carbon atoms and that $R_{19}$ be a straight or branched chain alkylene moiety of 1 to 4 carbon atoms. It is more preferred that $R_{19}$ be ethylene, i.e., —$CH_2$—$CH_2$—.

Other thioethers that are useful in the practice of the present invention can be of the structure:

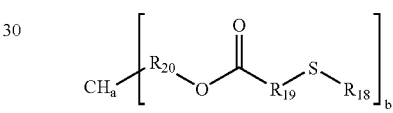

where a is 0 to 3, b is 1 to 4, and a+b=4, $R_{18}$ is as described above, and $R_{19}$ and $R_{20}$ are independently selected straight or branched chain alkylene moieties of 1 to 8 carbon atoms. It is preferred that $R_{19}$ and $R_{20}$ be independently selected straight or branched chain alkylene moieties of 1 to 4 carbon atoms. It is more preferred that $R_{20}$ be methylene, i.e., —$CH_2$—, and that $R_{19}$ be ethylene, i.e., —$CH_2$—$CH_2$—.

Preferred thioethers that are useful in the practice of the present invention are exemplified by products such as distearylthiodipropionate (Naugard DSTDP, Crompton Corporation), dilaurylthiodipropionate (Naugard DLTDP, Crompton Corporation), pentaerythritol tetrakis(β-laurylthiopropionate) (Seenox 412S, Crompton Corporation), and pentaerythritol octylthiopropionate (Naugard 2140, Crompton Corporation).

The optional co-stabilizer of the present invention can also be a trialkyl amine oxide, as, for example, GENOX™ EP(commercially available from Crompton Corporation) and described in U.S. Pat. Nos. 6,103,798; 5,922,794; 5,880,191; and 5,844,029.

Another co-stabilizer may be a hydroxylamine, as, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dioctylhydroxylamine, N,N-di-tert-butylhydroxylamine, N-cyclohexylhydroxylamine, N-cyclododecylhydroxylamine, N,N-dicyclohexylhydroxylamine, N,N-didecylhydroxylamine, N,N-di(coco alkyl)hydroxylamine, N,N-di($C_{20}$-$C_{22}$ alkyl)hydroxylamine, and N,N-dialkylhydroxylamine derived from hydrogenated tallow amine (i.e., N,N-di(tallow alkyl)hydroxylamine), as well as mixtures containing any of the foregoing.

The resulting stabilized polymer compositions of the invention may optionally also contain various conventional additives, such as the following:

1. UV absorbers and light stabilizers.
   1.1 2-(2'-hydroxyphenyl)-benzotriazoles, for example, the 5'-methyl-,3'5'-di-tert-butyl-,5'-tert-butyl-,5'(1,1,3 , 3-tetramethylbutyl)-,5-chloro-3',5'-di-tert-butyl-,5-chloro 3'-tert-butyl-5'-methyl-,3'-sec-butyl-5'-tert-butyl-,4'-octoxy,3',5'-di-tert-amyl-3',5'-bis-(α, α-dimethylbenzyl)-derivatives.
   1.2 2-Hydroxy-benzophenones, for example, the 4-hydroxy-4-methoxy-,4-octoxy,4-decloxy-,4-dodecyloxy-, 4-benzyloxy,4,2',4'-trihydroxy- and 2'-decylhydroxy-4, 4'-dimethoxy derivative.
   1.3 Esters of substituted and unsubstituted benzoic acids, for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butyl-phenyl-3,5-di-tert-butyl-4-hydroxybenzoate and hexadecyl-3,5-di-tert-butyl-4-hydroxybenzoate.
   1.4 Acrylates, for example, α-cyano-β, β-diphenylacrylic acid-ethyl ester or isooctyl ester, a-carbomethoxy-cinnamic acid methyl ester, α-cyano-β-methyl-p-methoxy-cinnamic acid methyl ester or butyl ester, a-carbomethoxy-p-methoxy-cinnamic acid methyl ester, N-(β-carbomethoxy-β-cyano-vinyl)-2-methyl-indoline.
   1.5 Nickel compounds, for example, nickel complexes of 2,2'-thiobis(4-(1,1,1,3-tetramethylbutyl)-phenol), such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands.
   1.6 Sterically hindered amines, for example bis(2,2,6,6-tetramethylpiperidyl)-sebacate, bis-(1,2,2,6,6-pentamethylpiperidyl)-sebacate, n-butyl-3,5-di-tert-butyl-4-hydroxybenzyl malonic acid bis(1,2,2,6,6,-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethylpiperazinone). These amines typically called HALS include butane teracarboxylic acid 2,2,6,6-tetramethyl piperidinol esters. Such amines include hydroxylamines derived from hindered amines, such as di(1-hydroxy-2,2,6,6-tetramethylpiperidin-4-yl)sebacate; 1-hydroxy 2,2,6,6-tetramethyl-4-benzoxypiperidine 1-hydroxy-2,2,6,6-tetramethyl-4-(3,5-di-tert-butyl-4-hydroxy hydrocinnamoyloxy)-piperdine; and N-(1-hydroxy-2,2,6,6-tetramethyl-piperidin-4-yl)-ε-caprolactam.
   1.7 Oxalic acid diamides, for example, 4,4'-dioctyloxyoxanilide, 2,2'-di-octyloxy-5',5'-di-tert-butyloxanilide, 2,2'-di-dodecyloxy-5',5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'ethyl-5,4-di-tert-butyloxanilide and mixtures of ortho- and para-methoxy as well as of o- and p-ethoxy-disubstituted oxanilides.

2. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzyliden-oxalic acid dihydrazide.

3. Phosphites and phosphonites, for example, triphenyl phosphite, diphenylalkyl phosphites, phenyldialkyl phosphites, tris(nonylphenyl)phosphite, trilauryl phosphite, trioctadecyl phosphite, distearyl pentaerythritol diphosphite, tris(2, 4-di-tert-butylphenyl)phosphite, diisodecyl pentaerythritol diphosphite, bis(2,4-di-tert-butylphenyl)pentaerythritol diphosphite, tristearyl sorbitol triphosphite, and tetrakis(2,4-di-tert-butylphenyl)4,4'-biphenylene diphosphonite.

4. Peroxide scavengers, for example, esters of β-thiodipropionic acid, for example, the lauryl, stearyl, myristyl, or tridecyl esters, mercaptobenzimidazole or the zinc salt of 2-mercaptobenzimidazole, zinc-dibutyldithiocaramate, dioctadecyldisulfide, pentaerythritoltetrakis-(β-dodecylmercapto)-propionate.

5. Polyamide stabilizers, for example, copper salts in combination with iodides and/or phosphorus compounds and salts of divalent manganese.

6. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, calcium stearate, calcium stearoyl lactate, calcium lactate, Zn stearate, Mg stearate, Na ricinoleate and K palmitate, antimony pyrocatecholate or zinc pyrocatecholate, including neutralizers such as hydrotalcites and synthetic hydrotalcites, and Li, Na, Mg, Ca, and aluminum hydroxy carbonates.

7. Nucleating agents, for example, 4-tert butylbenzoic acid, adipic acid, diphenylacetic acid, sodium salt of methylene bis-2,4-dibutylphenyl, cyclic phosphate esters, sorbitol tris-benzaldehyde acetal, and sodium salt of bis(2,4-di-t-butyl phenyl)phosphate.

8. Fillers and reinforcing agents, for example, calcium carbonate, silicates, glass fibers, asbestos, talc, kaolin, mica, barium sulfate, metal oxides and hydroxides, carbon black and graphite.

9. The compounds of the present invention may also be used in conjunction with aminoxy propanoate derivatives, such as methyl-3-(N,N-dibenzylaminoxy)propanoate; ethyl-3-(N,N-dibenzylaminoxy)propanonoate; 1,6-hexamethylene-bis(3-N,N-dibenzylaminoxy)proponoate); methyl-(2-(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

10. Other additives that may be employed in combination with the compounds of the present invention include, for example, plasticizers, epoxidized vegetable oils, such as epoxidized soybean oils, lubricants, emulsifiers, pigments, hydroxylamines, such as $R_2NOH$ wherein R is a $C_1$ to $C_{30}$ alkyl group, such as propyl or stearyl, optical brighteners, flameproofing agents, anti-static agents, blowing agents, and thiosynergists.

11. Nitrones, for example n-benzyl-α-phenyl nitrone, N-ethyl-α-methyl nitrone, N-octyl-α-heptyl nitrone, N-lauryl-α-undecyl nitrone, N-tetradecyl-α-tridecyl nitrone, N-hexadecyl-α-penta-decyl nitrone, n-octadecyl-α-heptadecylnitrone, N-hexadecyl-α-heptadecyl nitrone, N-octadecyl-α-pentadecy nitrone, N-heptadecyl-α-heptadecy nitrone, N-octadecyl-α-hexadecyl nitrone, and nitrone derived from N,N-dialkylhydroxylamine derived from hydrogenated tallow amine.

Polymeric particles may be coated with the present stabilizer compositions alone or in combination with other stabilizers for stabilization of the polymeric material. Particles may be spherical in shape and may be made by processes such as "Reactor Granule Technology" as disclosed in P. Galli and J. C. Halock, The Reactor Granule—A Unique Technology for the Production of a New Generation of Polymer Blends, Society of Plastics Engineers, Polyolefin III International Conference Feb. 24-27, 1991 and as disclosed in Pedrazzeth et al. U.S. Pat. No. 4,708,979, both of which are disclosed herein by reference. Particle formation may be achieved by support Ziegler-Natta Catalyst systems. Suitable commercial processes are known by the trademarks: Spheripol, Addipol, and Spherilene.

Olefin polymers may be produced by polymerization of olefins in the presence of Ziegler-Natta catalysts, optionally on supports, such as, but not limited to, $MgCl_2$, chromium salts and complexes thereof, optionally supported on silica or other materials. They may also be produced utilizing catalysts based on cyclopentadiene complexes of metals typically complexes of Ti and Zr.

The stabilizer compositions of the invention may be added to the polymer at any time prior to or during fabrication into articles and may be combined with the polymer by any of a variety of means known in the art, such as by preblending or by being fed directly into fabrication equipment.

Other ingredients that may be included in the compositions of the present invention include polymeric materials and other organic materials such as waxes, synthetic and petroleum dried lubricating oils and greases; animal oils such as, for example, fat, tallow, lard, cod liver oil, sperm oil; vegetable oil such as castor, linseed, peanut, cod seed, and the like; fuel oil, diesel oil, gasoline, and the like.

The advantages and the important features of the present invention will be more apparent from the following examples.

EXAMPLES

A novel phosphite stabilizer comprising both a neoalkanediol and a HALS (hindered amine light stabilizer) building block was synthesized in 89% yield (by weight) and with 98% purity (as measured by GC). The material was tested as a process stabilizer in poly(propylene) (PP) and high-density poly(ethylene) (HDPE) and was found to display excellent performance characteristics compared to a state-of the-art control, as determined by recording melt-flow stabilization.

Example 1

Preparation of 2,2,6,6-tetramethylpiperidin-4-ol-2-butyl-2-ethyl-1,3-propanediol-phosphite Into a one liter, four-necked, round-bottom reaction flask was weighed 69.2 grams (0.44 mole) of 2,2,6,6-tetramethylpiperidin-4-ol, 101.2 grams (1.00 mole) of triethylamine and 250 grams of toluene. The flask was equipped with a stir shaft and paddle, temperature probe, dropping funnel, and nitrogen inlet. The reaction mixture was placed under a nitrogen blanket. Most of the 2,2,6,6-tetramethylpiperidin-4-ol was soluble in the solvents at room temperature. 2-Butyl-2-ethyl-1,3-propanediol-chlorophosphite (89.9 grams (0.40 mole)) was weighed into the dropping funnel and then slowly added to the reaction flask. White solids formed immediately. The chlorophosphite was added at a rate of addition such that the reaction temperature stayed between 18 and 22° C. Occasional cooling with an ice bath was necessary to keep the temperature under control. The total addition time was 30 minutes. The ice bath was removed and the mixture was allowed to warm slowly to room temperature. Fifty grams of additional toluene was added to rinse the dropping funnel. The white solids were waxy and difficult to stir at 18° C. After two hours, the mixture was heated to a temperature of 65° C., and stirring was continued for another hour. The mixture was then heated to 80° C. and held there for one hour to ensure the reaction is complete. The mixture was cooled to room temperature and vacuum-filtered to remove any solids. The clear filtrate was evaporated to dryness under vacuum. The product was obtained as a pale yellow liquid. (Yield: 122.8 grams) (GC Purity: 98%). The product was analyzed by $^{31}$P-NMR analysis, giving a characteristic signal with a shift of δ=125 ppm.

Example 2

Process Stabilization of Poly(propylene)

This example illustrates the stabilizing effectiveness of 2,2,6,6-tetramethylpiperidin-4-ol-2-butyl-2-ethyl-1,3-propanediol-phosphite upon multipass extrusion in poly(propylene).

The base formulation comprised poly(propylene) powder (Profax 6501) containing 250 ppm calcium stearate and 250 ppm of tetrakis[methylene{3,5-di-tert-butyl-4-hydroxycinnamate}]methane (Naugard® 10), having a melt flow index of 3.8 measured at 230° C./2.16 kg.

Compound 2-2,2,6,6-tetramethylpiperidin-4-ol-2-butyl-2-ethyl-1,3-propanediol-phosphite—was incorporated into the base formulation at a level of 500 ppm, as was additional Naugard 10 at 500 ppm. The stabilized resin formulation was extruded from a ¾ inch diameter Brabender single-screw extruder at 50 rpm, with the four heating zones being set to the following temperatures: 240° C.; 250° C.; 260° C.; 270° C.

The extrudate was cooled by passing it through an ice water bath and was then pelletized. These pellets were re-extruded. After a third extrusion pass, the melt flow rate (in grams/10 min) was measured at 230° C./2.16 kg. A relatively small increase in melt flow index indicates insignificant polymer degradation, or good stabilization. The results are shown in Table 1.

TABLE 1

| Formulations of Example 2 | Extrusion Pass #3 Flow Rate (grams/10 minutes) |
|---|---|
| Base | 25.9 |
| Compound 2 | 7.7 |

The results from this study show that compound 2, which contained 2,2,6,6-tetramethylpiperidin-4-ol-2-butyl-2-ethyl-1,3-propanediol-phosphite, gave superior melt stabilization compared to the base formulation.

Example 3

Process Stabilization of Poly(ethylene)

This example illustrates the stabilizing effectiveness of 2,2,6,6-tetramethylpiperidin-4-ol-2-butyl-2-ethyl-1,3-propanediol-phosphite in poly(ethylene).

For a control experiment, 100 parts of poly(ethylene) (Finathene HDPE) was blended with 0.03 part of Naugard 10.

For Compound 3, 0.1 part of 2,2,6,6-tetramethylpiperidin-4-ol-2-butyl-2-ethyl-1,3-propanediol-phosphite was added to this mixture. The corresponding mixture was then added to a Brabender Plastograph at 220° C./50 rpm. While kneading in the mixing head continued, torque was continuously recorded. After an induction period, the polymer began to cross-link, which can be seen as a significant increase in torque. The results of the test are shown in Table 2, which shows the time in minutes for the induction period preceding the onset of torque. A relatively long induction time is indicative of superior stabilization.

TABLE 2

| Formulations of Example 3 | Plasticorder Test Induction Time (Minutes) |
|---|---|
| Control | 10 |
| Compound 3 | 55 |

The results of this test show that Compound 3, which comprised 2,2,6,6-tetramethylpiperidin-4-ol-2-butyl-2-ethyl-1,3-propanediol-phosphite, gave superior processing stability compared to the control.

In view of the many changes and modifications that can be made without departing from principles underlying the invention, reference should be made to the appended claims for an understanding of the scope of the protection to be afforded the invention.

What is claimed is:

1. A compound of the structure:

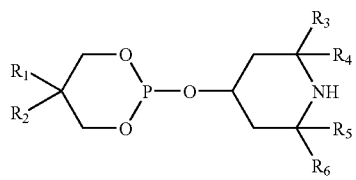

wherein $R_3$, $R_4$, $R_5$, and $R_6$ are independently selected alkyl groups, $R_1$ is ethyl, $R_2$ is butyl, and provided that said compound is a liquid at room temperature.

2. The compound of claim 1 wherein $R_3$, $R_4$, $R_5$, and $R_6$ are independently selected from the group consisting of straight chain and branched chain alkyl moieties of from 1 to 8 carbon atoms.

3. The compound of claim 2 wherein $R_3$, $R_4$, $R_5$, and $R_6$ are independently selected from the group consisting of straight chain and branched chain alkyl moieties of from 1 to 4 carbon atoms.

4. The compound of claim 3 wherein $R_3$, $R_4$, $R_5$, and $R_6$ are all the same.

5. The compound of claim 1 wherein said compound is 2,2,6,6-tetramethylpiperidin-4-ol-2-butyl-2-ethyl-1,3-propanediol-phosphite.

6. A stabilized composition comprising:
(A) a thermoplastic resin, and
(B) a stabilizing amount of:
 (1) a compound having the structure:

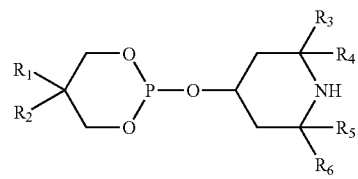

wherein $R_3$, $R_4$, $R_5$, and $R_6$ are independently selected alkyl groups, $R_1$ is ethyl, $R_2$ is butyl, and provided that said compound is a liquid at room temperature and, optionally,
 (2) a co-stabilizer selected from the group consisting of phenolics, aromatic amines, hydroxylamines, alkylamine-N-oxides, lactones, and thioethers.

7. The composition of claim 6 wherein $R_3$, $R_4$, $R_5$, and $R_6$ are independently selected from the group consisting of straight chain and branched chain alkyl moieties of from 1 to 8 carbon atoms.

8. The composition of claim 7 wherein $R_3$, $R_4$, $R_5$, and $R_6$ are independently selected from the group consisting of straight chain and branched chain alkyl moieties of from 1 to 4 carbon atoms.

9. The composition of claim 8 wherein $R_3$, $R_4$, $R_5$, and $R_6$ are all the same.

10. The composition of claim 6 wherein said compound is 2,2,6,6-tetramethylpiperidin-4-ol-2-butyl-2-ethyl-1,3-propanediol-phosphite.

11. A method for stabilizing a thermoplastic resin comprising adding to said resin a stabilizing amount of a stabilizer having the structure:

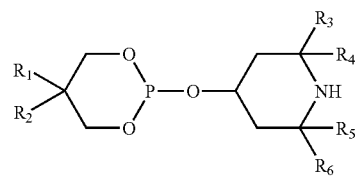

wherein $R_3$, $R_4$, $R_5$, and $R_6$ are independently selected alkyl groups, $R_1$ is ethyl $R_2$ is butyl, and provided that said compound is a liquid at room temperature.

12. The method of claim 11 wherein $R_3$, $R_4$, $R_5$, and $R_6$ are independently selected from the group consisting of straight chain and branched chain alkyl moieties of from 1 to 8 carbon atoms.

13. The method of claim 12 wherein $R_3$, $R_4$, $R_5$, and $R_6$ are independently selected from the group consisting of straight chain and branched chain alkyl moieties of from 1 to 4 carbon atoms.

14. The method of claim 13 wherein $R_3$, $R_4$, $R_5$, and $R_6$ are all the same.

15. The method of claim 12 wherein said stabilizer is 2,2,6,6-tetramethylpiperidin-4-ol-2-butyl-2-ethyl-1,3-propanediol-phosphite.

16. A method for the preparation of stabilizer having the structure:

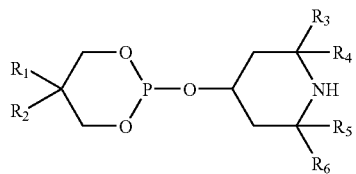

wherein $R_3$, $R_4$, $R_5$, and $R_6$ are independently selected alkyl groups, $R_1$ is ethyl, $R_2$ is butyl, and provided that said compound is a liquid at room temperature wherein the method comprises reacting a phosphorous trihalide with a tetraalkylpiperidinol and a 2-butyl-2-ethyl-1,3-propanediol.

17. The method of claim 16 wherein the 2-butyl-2-ethyl-1,3-propanediol is the first reacted with the phosphorous trihalide to yield the corresponding halophosphite, which is then reacted with the tetraalkylpiperidinol.

* * * * *